U S005643320A

United States Patent [19]
Lower et al.

[11] Patent Number: 5,643,320
[45] Date of Patent: Jul. 1, 1997

[54] SOFT TISSUE ANCHOR AND METHOD

[75] Inventors: Jerry L. Lower, Bourbon, Ind.; E. Marlowe Goble, Logan, Utah

[73] Assignee: DePuy Inc., Warsaw, Ind.

[21] Appl. No.: 403,070

[22] Filed: Mar. 13, 1995

[51] Int. Cl.$^6$ ................................................. A61B 17/04
[52] U.S. Cl. .......................... 606/232; 606/139; 606/144; 606/73; 606/104
[58] Field of Search ................................. 606/72, 73, 232, 606/75, 104, 65, 187, 139, 144; 411/388, 389, 393, 402

[56] References Cited

U.S. PATENT DOCUMENTS

| | | |
|---|---|---|
| 4,590,928 | 5/1986 | Hunt et al. . |
| 4,592,346 | 6/1986 | Jurgutis . |
| 4,632,100 | 12/1986 | Somers et al. . |
| 4,711,234 | 12/1987 | Vives et al. . |
| 4,738,255 | 4/1988 | Goble et al. . |
| 4,779,616 | 10/1988 | Johnson . |
| 4,793,335 | 12/1988 | Frey et al. . |
| 4,946,468 | 8/1990 | Li ............................. 606/232 |
| 4,960,420 | 10/1990 | Goble et al. ................. 606/72 |
| 4,988,351 | 1/1991 | Paulos et al. ................ 606/72 |
| 4,997,433 | 3/1991 | Goble et al. ................. 606/72 |
| 5,013,316 | 5/1991 | Goble et al. ................. 606/64 |
| 5,037,426 | 8/1991 | Goble et al. ................. 606/96 |
| 5,041,129 | 8/1991 | Hayhurst et al. ............ 606/232 |
| 5,064,425 | 11/1991 | Branemark et al. ......... 606/72 |
| 5,071,420 | 12/1991 | Paulos et al. ................ 606/99 |
| 5,100,417 | 3/1992 | Cerier et al. ................ 606/232 |
| 5,102,421 | 4/1992 | Anspach, Jr. ............... 606/232 |

(List continued on next page.)

FOREIGN PATENT DOCUMENTS

| | | | |
|---|---|---|---|
| 3538593 | 5/1987 | Germany ................. 606/73 |
| 827050 | 5/1981 | U.S.S.R. .................. 606/73 |
| 88/09157 | 12/1988 | WIPO .................... 606/232 |

OTHER PUBLICATIONS

"Technique for Using The Tag™ Tissue Anchor—Rod Style", Mitek Surgical Products, Inc., brochure, 4 pages, 1990.
"The Biofix" System, Total Absorbable, Totally Easy, Totally Acufex*, Acufex Microsurgical, Inc., brochure, 6 pages, 1990.
"Fracture Management—State™ Soft Tissue attachment Device", Zimmer Catalog No. 2344–10, 4 pages, 1989.
"Mikek GII Snap", Mitek Surgical Products, Inc., brochure, 6 pages, 190.
"Acufex introduces TAG™: the system for secure tissue re-attachment.", Acufex Microsurgical, Inc., brochure, 2 pages.
"Technique for Using The Tag™ Tissue Anchor—Wedge Style", Acufex Microsurgical, Inc., brochure, 6 pages, date unknown.
Richmond et al., "Modification of the Blanket reconstruction with a suture anchor," The American Journal of Sports Medicine, vol. 19, No. 4, pp. 343–346.

*Primary Examiner*—Guy V. Tucker
*Assistant Examiner*—Patrick W. Rasche
*Attorney, Agent, or Firm*—Barnes & Thornburg

[57] ABSTRACT

A preassembled disposable driver and suture anchor are provided for threaded engagement into a bone to provide an attachment point for soft tissue. The anchor is formed to have an externally threaded body portion for engaging the bone, a distal end portion, and a proximal end portion. When the anchor is threaded into an opening in a bone, the distal end portion is adjacent a bottom of the opening and the proximal end portion is adjacent a mouth of the opening. A suture is attached to said anchor having free ends extending outwardly from the bone opening. The driver is elongated and has a distal end which engages the proximal end of the anchor and a proximal end for gripping by the surgeon. The driver also has a slot for receiving the suture which extends away from the anchor. The distal end portion of the driver is radially enlarged relative to the body portion of the anchor to engage the bone surrounding the mouth of the opening to limit the internal advancement of the driver such that further rotation and threading of the anchor into the bone by the driver will separate the anchor from the driver.

42 Claims, 5 Drawing Sheets

U.S. PATENT DOCUMENTS

| | | | |
|---|---|---|---|
| 5,129,906 | 7/1992 | Ross et al. | 606/77 |
| 5,139,520 | 8/1992 | Rosenberg | 606/87 |
| 5,141,520 | 8/1992 | Goble et al. | 606/232 |
| 5,156,616 | 10/1992 | Meadows et al. | 60/232 |
| 5,207,679 | 5/1993 | Li | 606/72 |
| 5,211,650 | 5/1993 | Noda | 606/139 |
| 5,224,946 | 7/1993 | Hayhurst et al. | 606/72 |
| 5,236,445 | 8/1993 | Hayhurst et al. | 606/232 |
| 5,246,441 | 9/1993 | Ross et al. | 606/72 |
| 5,258,016 | 11/1993 | DiPoto et al. | 606/232 |
| 5,268,001 | 12/1993 | Nicholson et al. | 606/72 |
| 5,324,308 | 6/1994 | Pierce | 606/232 |
| 5,354,298 | 10/1994 | Lee et al. | 606/72 |
| 5,370,662 | 12/1994 | Stone et al. | 606/75 |
| 5,411,523 | 5/1995 | Goble | 606/232 |

SOFT TISSUE ANCHOR AND METHOD

BACKGROUND AND SUMMARY OF THE INVENTION

This invention relates to soft tissue anchors for securing a ligament or tendon or the like to a bone surface during a repair or replacement surgical procedure. More particularly, this invention relates to an anchor which may be placed in an opening in a bone to serve as an attachment point for soft tissue, the anchor having a suture or other means for engaging the soft tissue. Further, the present invention relates to a driver for inserting the anchor with the anchor and driver being proportioned and designed to be used in a facile and safe manner in a confined space. Still further, the present invention relates to a method for using the anchor and driver of the present invention.

PRIOR ART

There are many types of soft tissue anchors, including suture anchors, in the prior art. There are several prior art approaches for clamping or tacking soft tissues such as a ligament onto a prepared bone surface. The present invention relates to the type of tissue anchor which is threaded or otherwise inserted into a small opening or hole drilled or otherwise formed into the bone to serve as an anchor support. Typically, an anchor with sutures firmly attached to it is threaded or otherwise tightly inserted into an opening in the bone to position the free ends of the suture as means for engaging the soft tissue and holding it against the bone. The suture free ends are then stitched about and through the soft tissue and tied by the surgeon to attach the tissue securely to the bone.

The present invention is an improvement over the prior art anchors, including suture anchors, because it provides both an anchor and a disposable driver for the anchor which are preassembled to be used in a facile and safe insertion procedure in very confined areas such as often encountered in arthroscopy.

BRIEF SUMMARY OF THE INVENTION

It is an object of the present invention, therefore, to provide a preassembled disposable driver and anchor for threaded engagement into a bone to provide an attachment point for soft tissue, the distal end portion of the driver being radially enlarged relative to the body portion of the anchor to engage the bone surrounding the mouth of the opening to limit the internal advancement of the driver such that further rotation and threading of the anchor into the bone by the driver will separate the anchor from the driver. In this fashion, the anchor will be properly placed within the opening in the bone to be secured in the opening and to provide a means for engaging the soft tissue to hold it against the bone surrounding the opening. It will be appreciated as this description progresses that the anchor and the driver are proportioned and designed such that, when they are used with an internally-threaded bone opening which is also proportioned and designed to receive the anchor, the anchor will be inserted into the opening in a facile and safe manner without damaging the internal threads in the bone opening.

In the illustrative and preferred embodiment, the means for engaging the soft tissue may be a suture which is attached to the anchor to have free ends extending outwardly from the mouth of the opening for engaging the soft tissue. It will be appreciated that use of anchored sutures by orthopaedic surgeons is well known and need not be discussed herein. In another illustrative and preferred embodiment, the engaging means may be a post or spike upon which the soft tissue is engaged. For the suture embodiment, the suture may preferably be loosely threaded through axially-extending passageways in the anchor so that the free ends of the suture may be adjusted to equalize the tension applied to the suture by the attachment of the soft tissue.

Another object of the present invention is to provide a preassembled disposable driver and suture anchor for threaded engagement into a drilled and threaded opening in a bone to provide an attachment point for soft tissue to the bone with the bone opening being deeper than the axial length of the anchor and the anchor being formed to have an externally threaded body portion for engaging the bone, distal end portion, and a proximal end portion such that, when the anchor is threaded into the threaded opening in the bone, the distal end portion is adjacent and spaced apart from the bottom of the opening leaving an internal cavity and the proximal end portion is adjacent a mouth of the opening. The anchor preferably has a pair of suture openings extending longitudinally from the proximal end to the distal end, and a suture extends into one of the pair of openings into the internal cavity and back out through the other of the pair of openings to have opposite free ends extending outwardly from the proximal end of the anchor and movable within the pair of openings to equalize the tension in the suture when a soft tissue load is placed on the suture. The driver for this suture anchor is elongated to have a distal end including means for drivingly engaging the proximal end of the anchor and a proximal end for gripping by the surgeon.

It is another object of the present invention to provide such an anchor which is configured to form a male head at the proximal end of the anchor while the distal end of the driver is formed to include a female socket opening configured to receive the male head to provide a driving connection between the driver and the anchor. In one preferred embodiment of the present invention, there is a press fit between the male head on the anchor and the female socket on the driver such that the anchor will stay attached to the driver until it is disengaged by the aforedescribed engagement of the driver with the bone surrounding the opening to limit the internal advancement of the driver. The male head on the anchor and the female socket on the driver may have a square shape. The male head may include four corners which are threaded when the body portion of the anchor is threaded. In one preferred embodiment of the invention, the threaded body portion of the anchor includes threads having a major diameter and a minor diameter, the head of the anchor having a diameter larger than the minor diameter of the threads on the main body portion.

In addition to or in place of the press fit between the anchor and the driver, the driver may include means for holding the free ends of the suture in tension also to hold the anchor on the driver.

Another object of the present invention is to provide such an anchor which is absorbable. A variety of materials may be absorbable into the bone and the host body including absorbable plastic materials.

Still another object of the present invention is to provide a threaded suture anchor for attaching soft tissue to a bone with the anchor being threaded into an opening in the bone to be left there after the surgery and after the soft tissue for which it is an anchor has reattached itself to the bone. Some plastic materials will be absorbed into the bone ultimately and the opening in the bone will close. It will be appreciated that such plastic materials may well be rather structurally weak, for instance, as compared to metal or other material from which anchors may be made. In some cases, it may be preferable to have an absorbable anchor with a suture which is not absorbable.

Further, it will be appreciated that the threaded opening in the bone is such that the threads need to be protected and engaged properly by the anchor so as not to strip the threads in the bone. In the present invention, the bone opening or hole is drilled and tapped in such a fashion that the anchor and driver of the present invention can be used threadedly to insert the anchor into the opening so as not unduly to over-stress either the threads on the anchor or the threads in the bone. It is an object of the present invention, therefore, to provide a bone anchor and a specially-formed driver and a method for using the anchor and driver threadedly to insert the anchor into the bone opening in a facile and safe manner.

The method for attaching soft tissue to a bone using an anchor having an externally-threaded body portion in accordance with the present invention comprises the steps of first drilling a hole into the bone to a first predetermined depth with a spot faced, dressed area cut in the face of the bone about an outer periphery of the hole to provide an attachment location for the soft tissue; tapping the hole to provide internal threads to a second depth less than the first depth; and then inserting the externally-threaded anchor, having an axial length less than the first predetermined depth and a threaded length less than the second predetermined depth into the hole so that a distal end of the anchor is spaced apart from the bottom of the hole to provide an internal cavity and a proximal end of the anchor is disposed generally within the hole. This anchor carries means for engaging the soft tissue to position the soft tissue against the spot faced, dressed area around the hole. It will be appreciated that, in some cases, the drilling and tapping step may be accomplished at the same time using the same tool or combination of tools. The method may also include forming a countersink around the mouth of the hole with the dressed area cut around the countersink so that the proximal end of the anchor is disposed generally within the countersink. This method may also include using a driver to rotate the anchor with the driver having a larger diameter than the anchor so that the driver engages the countersink to block internal advancement of the driver so that further rotation and threading of the anchor into the bone by the driver automatically separates the driver from the inserted anchor. In this fashion, the anchor is properly positioned within the threaded hole within the bone so as not to stress the threads either on the anchor or in the bone.

Other objects and features of the present invention will become apparent as this description progresses.

DETAILED DESCRIPTION OF THE DRAWINGS

Figures 1, 1A, 2, 2A:
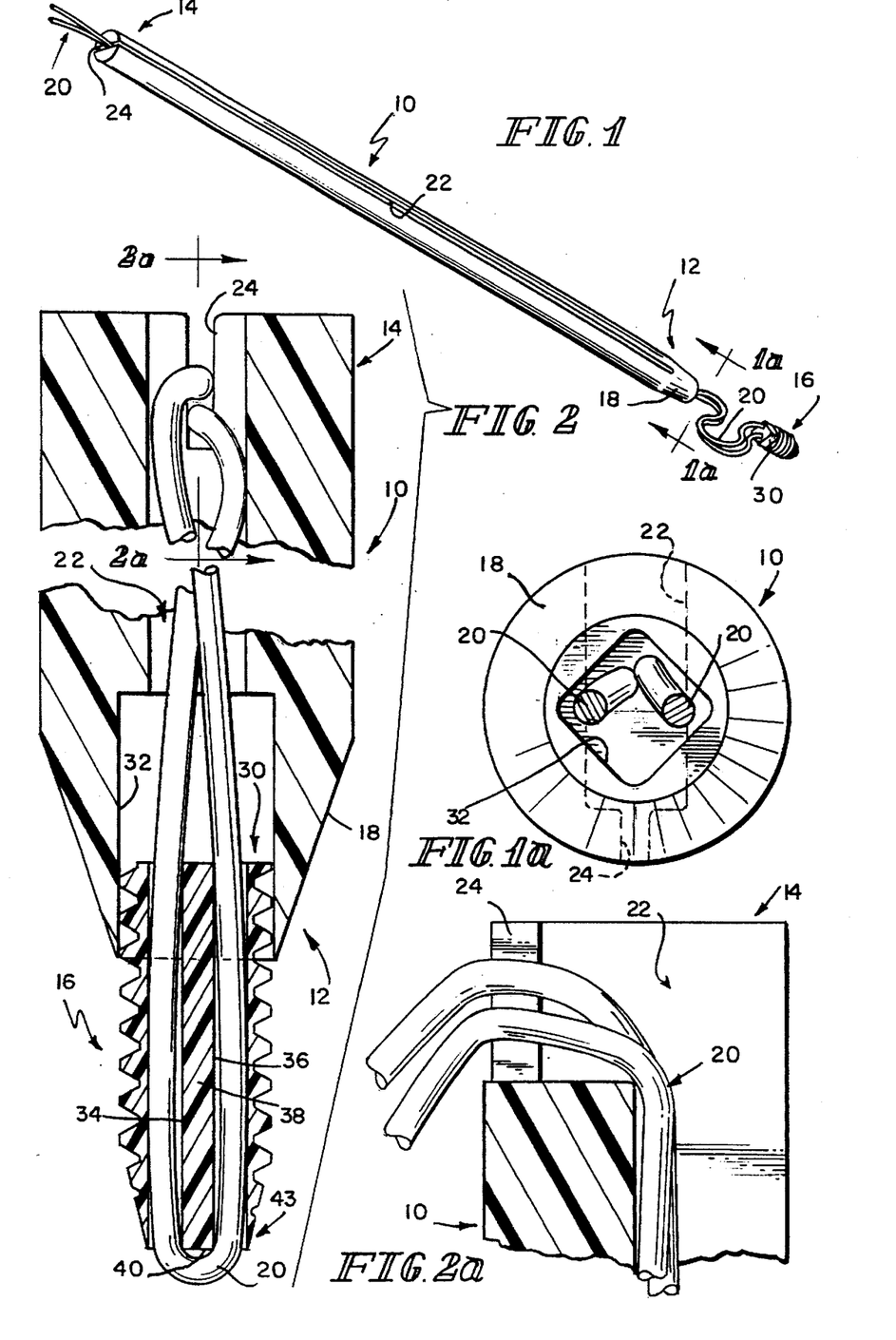
FIG. 1 is a perspective view of the driver and the anchor of the present invention showing the suture extending from the anchor rearwardly through the driver.
FIG. 1a is a sectional view taken along lines 1a—1a of FIG. 1 illustrating details of the configuration of the driver.
FIG. 2 is an enlarged, fragmentary sectional view showing the anchor and the means for driving the anchor at the proximal end of the anchor and the distal end of the driver.
FIG. 2a is a sectional view taken along lines 2a—2a of FIG. 2 illustrating further details of the distal end of the driver.

Turning to FIG. 1, it will be seen that the driver 10 may be elongated in a somewhat pencil-like fashion to have a distal end or end portion 12 and a proximal end or end portion 14. The distal end 12 engages an anchor 16 to drive the anchor when the driver 10 is rotated by the surgeon. Of course, the surgeon will grasp the proximal end 14 of the driver 10 to rotate the driver about its axis. The illustrative distal end 12 has a frusto-conical exterior 18 which is shaped to be received in a countersink in the bone opening to be described hereinafter. The body of the driver 10 may be tubular such that the suture 20 may extend outwardly from the anchor 16 back through the body of the driver. Alternatively, as shown in FIG. 1, the driver may have an elongated slot 22 extending axially throughout the length of the body to receive the suture 20. The proximal end 14 of the driver 10 may have a radially-extending slot 24 which tightly grips and engages the suture 20 so that the suture can be tensioned to hold the anchor 16 into engagement with the driver 10.

The illustrative anchor 16 is provided with a male head 30 at its proximal end 39 to be press fit into a female socket 32 formed in the distal end 12 or driver 10. FIG. 2 shows this relationship very well and shows the suture 20 leading from the anchor 16 outwardly into the driver 10. The suture 20 in the illustrative and preferred embodiment is threaded loosely through axially and longitudinally-extending passageways 34, 36 which define a web 38 therebetween having a rounded web or web portion 40 at the distal end 43 of the anchor 16. This web portion 40 is preferably rounded and smooth as illustrated so that it will not provide a stress point or stress concentration for potential suture or anchor 16 breakage.

The anchor 16 may be made from a wide variety of materials including a wide variety of polymers. A polymer anchor may be useful because of its translucency to X-ray and non-interference to magnetic resonance imaging (MRI) scanning. The illustrative and preferred anchor 16 of the present invention was designed to be used with a pre-drilled and tapped opening in the bone. The invention contemplates that a properly drilled and tapped hole or opening in the bone will provide optimum pull-out strength while the inserting step (threaded engagement) will require a minimal amount of torque. It will be noted that the philosophy for designing polymer threads is different than designing metal bone screw threads. In soft cancellous or osteoporotic bone, the strength of the screw's threads do not matter, because the bone will shear in pull-out at the major diameter. The shear strength of most polymers that might be usable for anchor material is less than that of cortical bone, i.e., the tough exterior portion of the bone, while the elasticity of the polymers is many times greater than the elasticity of the cortical bone. It has been determined that the presently preferred thread shape is a Conventional Unified Screw Thread (thread formed on most metal machine screws) to maximize the strength of the flexible lower strength polymer threads in bones. This Conventional Unified Screw Thread shape, very much in contrast to the typical bone screw thread, will distribute the shear loads proportionately in the vicinity of the pitch diameter of the threads.

The anchor 16 may be made from a variety of materials including plastic materials which may or may not be absorbable. An absorbable plastic material may be a polylactic acid (PLA), one of which is known in the trade as Poly L-Lactide, or may be a polyglycolic acid (PGA). It is presently believed that the PLA material has promise as an absorbable anchor material. Plastic materials which are not absorbable may be of ultra high molecular weight polyethylene. One such material is sold as Hylamer-M and has significant potential. Another possible material is known as Delrin. Delrin tends to be a more brittle material than polyethylene and it may be notch sensitive or subject to stress risers. In testing, Delrin did not perform as well as other materials and seemed to be deteriorated as a result of the radiation sterilization process. The Poly-L Lactide material, without sterilization, had good pull-out strength in testing, but the effect of sterilization has yet to be determined. In testing to date, the Hylamer-M material is the best suited non-absorbable polymer material from which to make a suture anchor 16.

It will be appreciated that a wide variety of suture materials may be used with the anchor 16 of the present invention, leaving it to the orthopaedic surgeon to make a selection for suture material. It is contemplated by the present invention that each disposable driver 10 will be assembled to an anchor 16 as shown in FIG. 2 with a selected suture already threaded into the anchor as shown in FIG. 2 to extend through the proximal end 14 of the driver 10. It is contemplated that a plurality of sterilized packages of preassembled drivers 10 and anchors 16 with appropriate sutures 20 will be provided to a surgeon for selective use in the surgery. The driver 10 may be made from any suitable plastic material which can be molded and then subsequently cleaned and sterilized to have the appropriate mechanical strength for holding the anchor 16 and driving the anchor into the threaded opening in the bone.

Figures 3, 4, 5, 6, 7, 8:
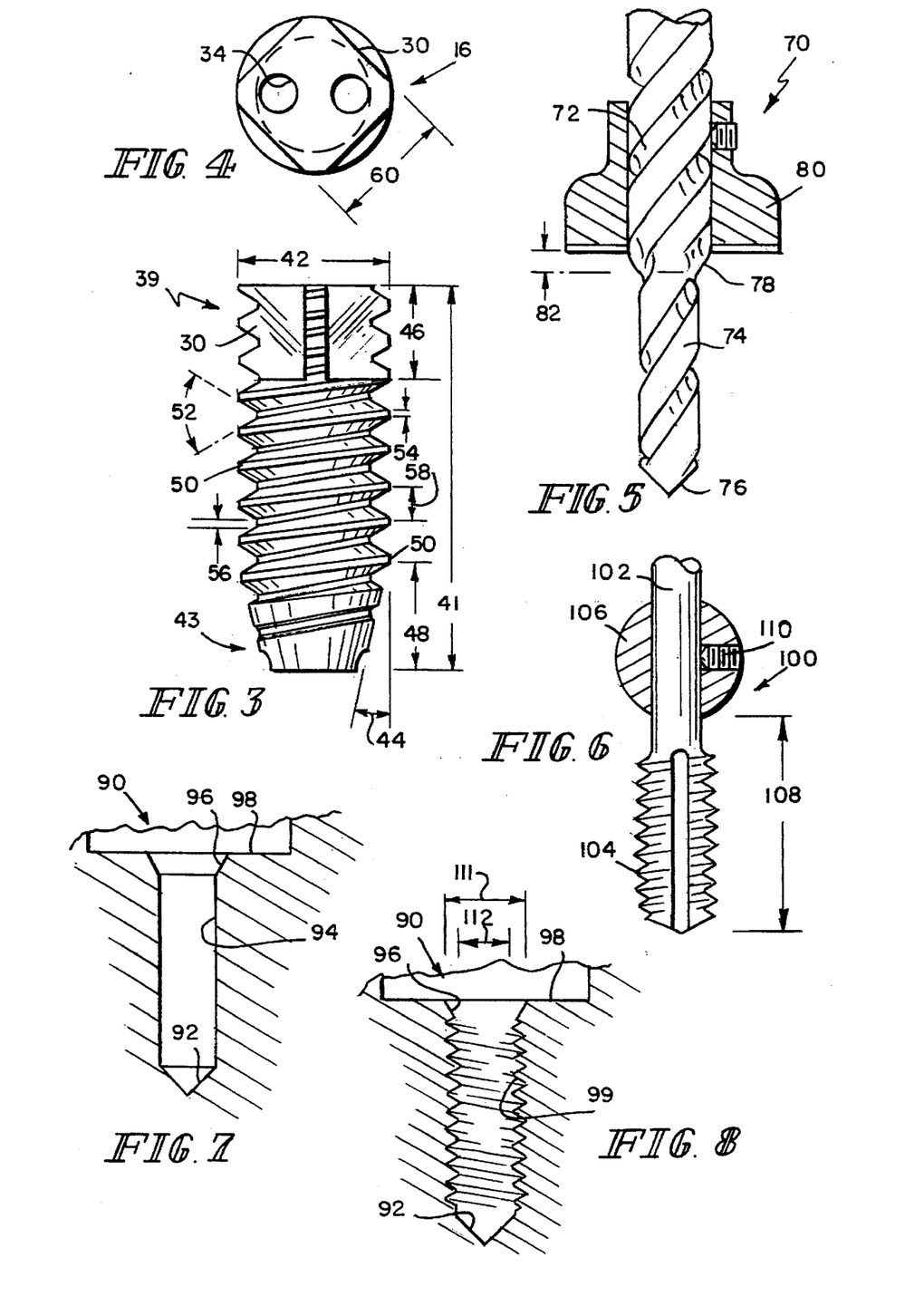
FIG. 3 is a plan view of the anchor showing the thread structure.
FIG. 4 is an end view of the anchor showing the male head which is pressed into the female socket on the driver and also showing the axial passageways for receiving the suture.
FIG. 5 shows a step drill for use in drilling the bone opening for receiving the anchor.
FIG. 6 shows a tapping tool for use in tapping the bone opening.
FIG. 7 shows a drilled and dressed opening in a bone.
FIG. 8 shows the threading in the opening which is accomplished using the tap tool shown in FIG. 6.

Turning now to FIGS. 3 and 4, it will be seen that the anchor 16 is illustrated as having a length 41 and an outer diameter (major diameter) 42. The distal end 43 is initially machined or otherwise formed to be tapered, for instance 15°, as shown by the angle 44. The head 30 is shown in FIG. 4 as having a generally square transverse cross section with rounded corners, the head having an axial length indicated at 46 in FIG. 3. The distal end portion of the anchor 16 is indicated at 48, i.e., the 15° tapered portion. The threads 50 are cut to be the machine threads described above to have the thread angle 52 (typically 60°), the major diameter as indicated at 42 with the outer flat on the thread being indicated at 54 on the major diameter and the internal flat on the minor diameter being indicated at 56. In a typical ligament anchor, the length 41 is about 10 mm while the major diameter 42 is about 2 mm to about 4 mm. The axial depth 46 of the head is about 2 mm while the pitch 58 between the threads is about 1 mm.

As best seen in FIGS. 2 and 3, the head 30, which may have a flat dimension 60 as shown in FIG. 4, is designed to be press fit upwardly into the female socket 32 best illustrated in FIG. 1a for the full axial length 46 of the head 30 in the preassembled state. It is believed that a device in accordance with the present invention can be provided such that the press fit between the head 30 and the socket 32 will be sufficient to keep the anchor 16 attached to the driver 10 so that the surgeon may simply hold onto the proximal end 14 of the driver and insert the anchor. To supplement the press fit, if such supplementing is required, the suture 20 may be tensioned and pulled into the tight slot 24 at the proximal end 14 of the driver 10 further to assist in holding the driving connection between the anchor 16 and the driver 10. The design, of course, is to prevent the anchor 16 from dropping off the driver 10 during the surgery process before it is inserted into the threaded opening in the bone. Further, in viewing FIG. 2, it will be seen that the distal end portion 12 of the driver 10 is radially larger in diameter than the anchor 16, particularly at the frusto-conical portion 18 which engages into the countersink of the bone opening as will be discussed hereinafter.

FIG. 5 shows a step drill 70 to be used by an orthopaedic surgeon to drill the bone hole or opening for the anchor 16 of the present invention. The step drill 70 is provided with a shaft 72 with a drill bit portion 74 including the drill tip 76. A predetermined distance from the drill tip 76, a countersink cutting portion 78 is provided. A spot face cutter 80 is provided a predetermined distance 82 axially back of the countersink cutter 78. This step drill 70 is used to form the drilled and dressed opening 90 shown in FIG. 7 to provide an opening having an inner end or bottom 92, an internal wall 94 to be tapped or threaded, a countersink 96 corresponding to the drill countersink portion 78 and a spot faced, dressed area 98 which will cause blood flow to enhance the attachment of the soft tissue against the bone.

FIG. 6 shows an appropriate tapping tool 100 including a shaft 102 upon which the thread cutting teeth 104 are formed. The tool 100 includes a depth stop 106 which engages the outer surface of the bone to control the depth of the cutting portion 104 to a predetermined depth indicated at 108. The stop 106 may be axially adjustable by the adjustment mechanism shown at 110 to vary the depth 108.

FIG. 8 illustrates the opening of FIG. 7 with the threads 99 formed by the tapping tool 100. As indicated in FIG. 8, the threads 99 in the bone opening 90 may be cut to have a major diameter 111 and a minor diameter 112. It is presently contemplated that the anchor 16 threads 50 and the threads 99 in the opening 90 will be cut such that there is approximately 50–75% thread engagement of the anchor threads to the opening threads. The countersink 96 may be about 0.5 mm in depth while the spot face 98 depth will generally be left to the doctor, but be sufficient to provide a bleeding surface for attachment of soft tissue. It will be appreciated that the distance from the tip of the drill 76 to the spot face 80 will be a fixed distance with each drill 70 and that with the stop 106 properly located on the tool 100, the threads formed in the bone will be at a precise location in the opening to receive the anchor 16.

Figures 9, 10:
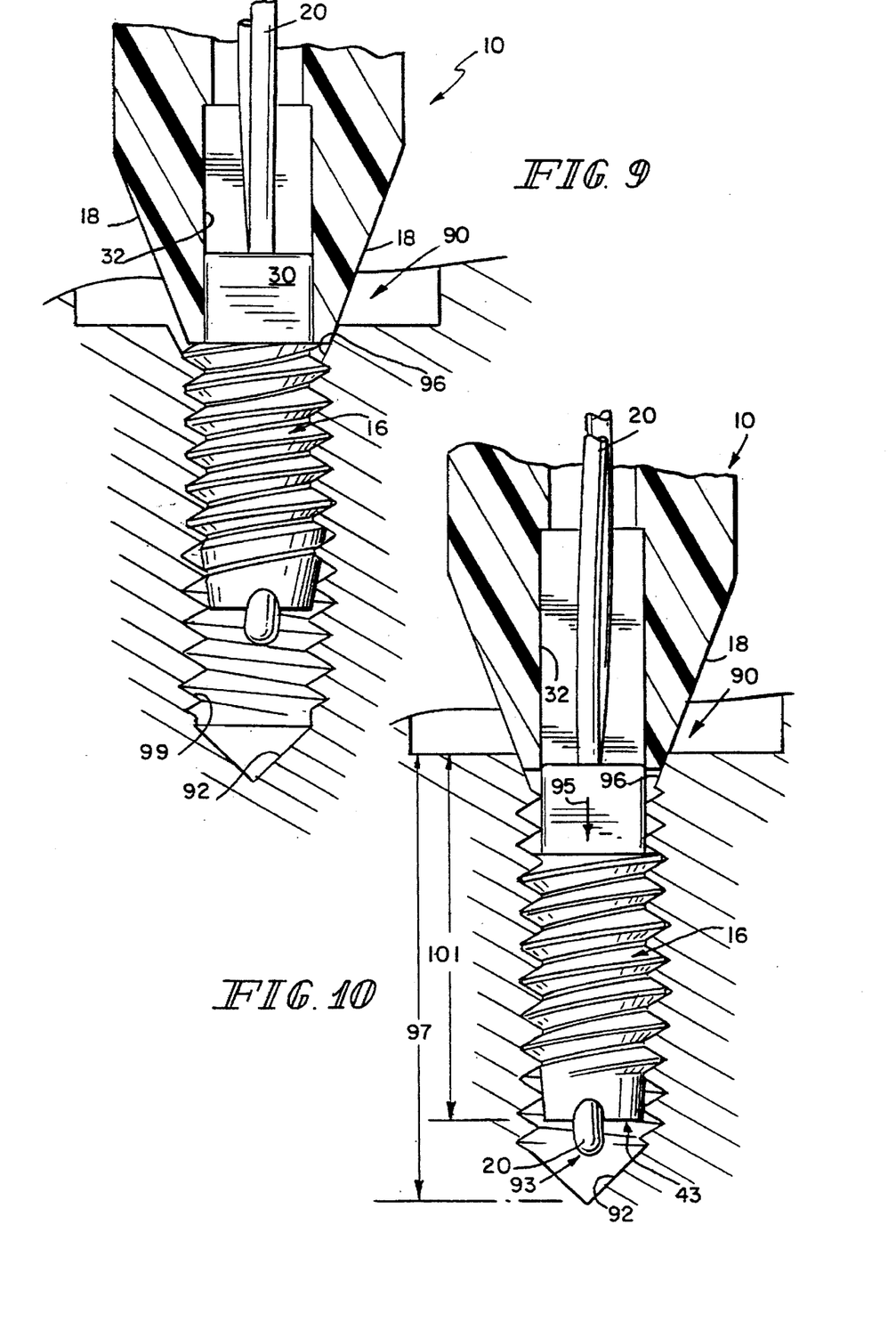
FIG. 9 is an enlarged fragmentary sectional view showing the driver and the anchor connected together with the driver in a position further to advance the anchor into the threaded bone opening when the distal end of the driver is engaged with the bone surrounding the bone opening.
FIG. 10 is a view similar to FIG. 9 but showing the advancement of the anchor away from the driver further into the bone opening to separate the anchor from the driver.

The relationship between the anchor 16 and the opening 90 with the driver 10 is best seen in FIGS. 9 and 10. Essentially, the anchor 16 is initially turned and driven into the threaded opening 90 to the point that the distal end 12 of the driver 10 engages the bone (the frusto-conical portion 18 of the distal end 12 of the driver 10 engages into the countersink 96). At that point, of course, the driver 10 will not further advance inwardly into the opening 90. Specifically, as mentioned above, the driver 10 has a radial dimension larger than the anchor such that it engages the mouth around the opening to stop axial inward movement of the driver 10. Further rotation of the driver at this point will rotate the anchor 16 to advance the anchor 16 into the opening 90 away from the driver 10, thereby to separate the driving connection between the head 30 and the socket 32. Even with the suture 20 holding the anchor 16 in a somewhat tensioned fashion, the anchor 16 will advance away from the driver 10 to go to a precise depth location in the opening 90. In this fashion, the anchor 16 will be precisely located in the opening 90 without stripping the threads cut in the bone or damaging the threads on the anchor 16. FIG. 9 illustrates conical surface 18 of driver 10 in engagement with countersink 96 of opening 90. Head 30 of anchor 16 is still in its original position inside socket 32 of driver 10. As driver 10 continues to rotate, driver 10 remains in its initial position of FIG. 9, but anchor 11 continues to move in the direction of arrow 95 in FIG. 10 until head 30 becomes disengaged from socket 32 of driver 10.

The depth of opening 90 is illustrated by dimension 97, while the insertion depth of the anchor 16 is illustrated by dimension 101. Therefore, as illustrated in FIG. 10, distal end 43 of anchor 16 is spaced apart from bottom surface 92 of opening 90 to provide an internal cavity 93 therebetween.

Figures 11, 12:
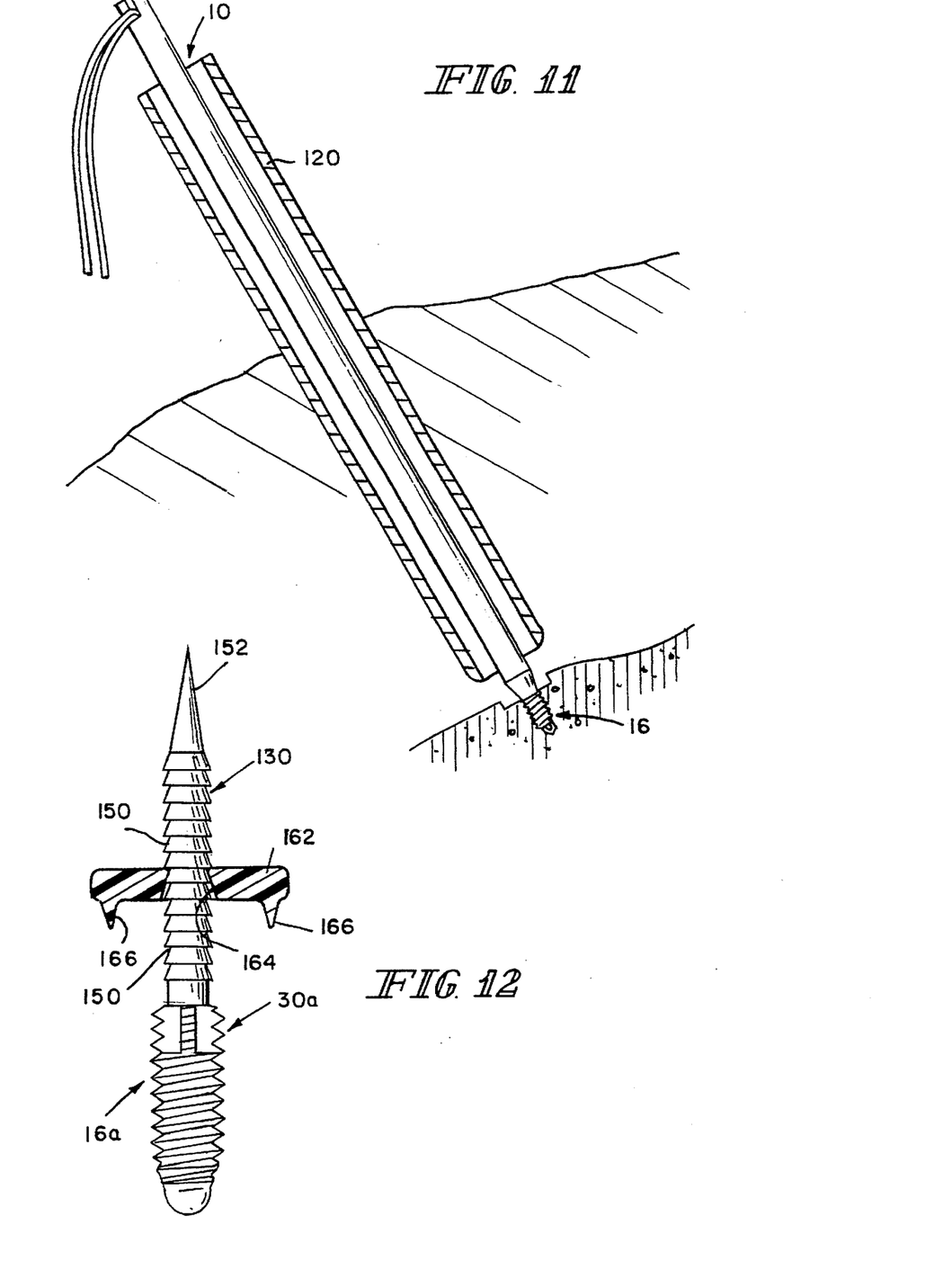
FIG. 11 is a diagrammatic view illustrating the driver and anchor of the present invention used with an introducer sleeve which may be conventionally inserted using a typical trocar-introducer device.
FIG. 12 is a plan view of another embodiment of the present invention utilizing a soft tissue post to engage the soft tissue rather than a suture as shown in FIGS. 1–11.
Figure 13:
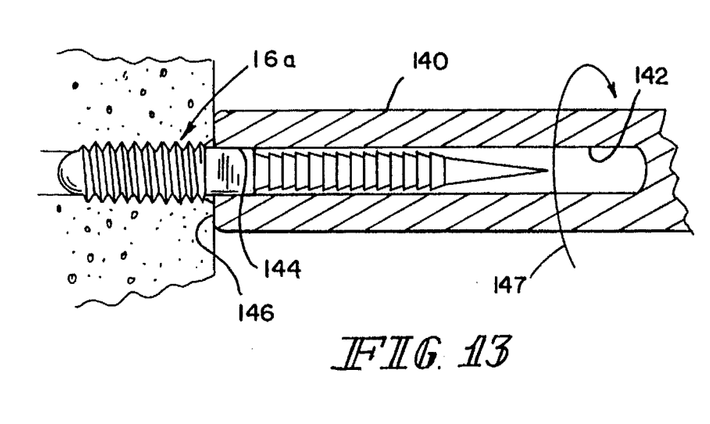
FIG. 13 shows a driver and the anchoring device of FIG. 12.

In FIG. 11, the driver 10 and accompanying anchor 16 are shown being inserted through an introducer tube or cannula 120 that previously has been used with a trocar to provide a passageway for inserting the driver and anchor. It will be appreciated that use of a trocar may well be required in some surgery where the ligament reattachment is rather difficult to reach such as in arthroscopy surgery. It will further be appreciated that the anchor 16 and driver 10 may be of relatively small diameter, such as about 2 mm to about 4.5 mm to be used in arthroscopy surgery.

Figure 14:
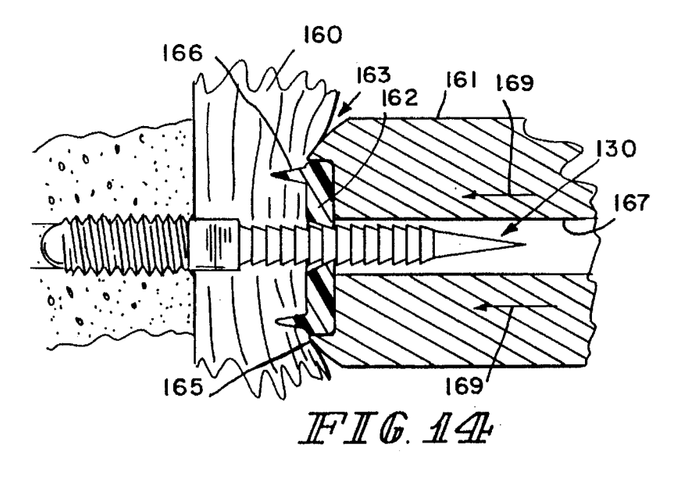
FIG. 14 shows the use of a tool to push a locking washer over the teeth of the post to engage the soft tissue against the bone.

In FIGS. 12–16, an anchor 16a is shown, and this anchor has a soft tissue post or stud 130 extending axially outwardly from the anchor 16a. The anchor 16a is provided with a driving head 30a corresponding to the head 30 in FIGS. 1–11. Essentially, a tubular driver 140 illustrated in FIG. 13 with a central, axially-extending opening 142 for receiving the post 130 is provided, the driver 140 having jaws 144 for receiving and engaging the head 30a. The driver 140 has a distal face 146 which engages the bone to limit the movement of the driver 140 to the left as viewed in FIG. 13, i.e., into the opening in the bone. Further rotation of the driver 140 and the anchor 16a in the direction of arrow 147, of course, moves the anchor 16a to the left as viewed in FIG. 13 as discussed previously. The post 130 has teeth 150 on it and a sharpened point 152. Once the anchor 16a is fixed into the bone, and the tool 140 is removed, the spiked post with its teeth 150 may be penetrated through the soft tissue. Then, a washer 162 which is made to engage over the teeth 150 and move in only one direction, i.e., to the left as viewed in FIG. 14, is provided.

Figure 15:
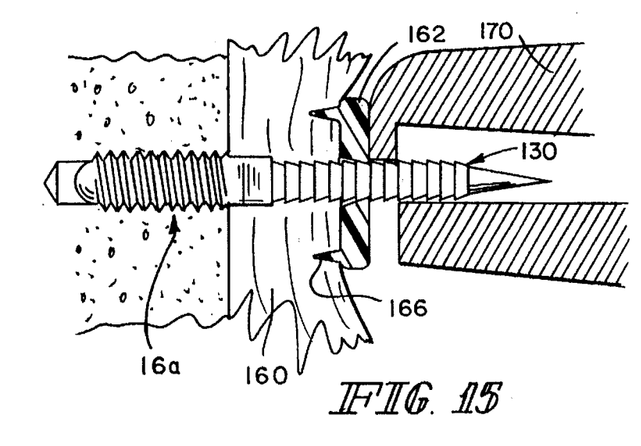
FIG. 15 shows the use of a shear-action cutter to cut off the outer end of the post, i.e., the sharpened end which initially penetrates through the soft tissue.
Figure 16:
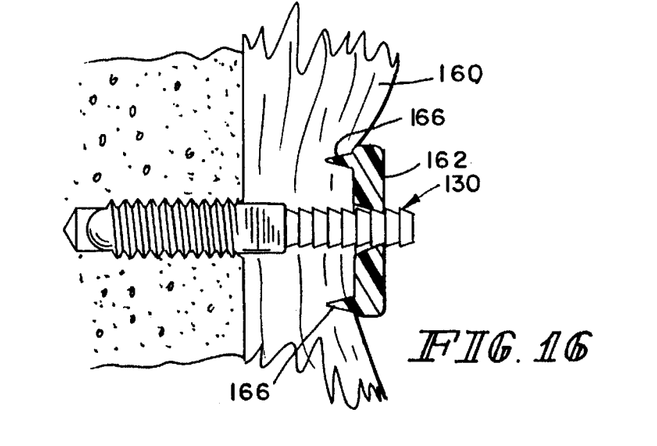
FIG. 16 shows the device of FIG. 12 utilized to attach the soft tissue to the bone.

This washer 162 has a central opening 164 for fitting over the teeth 150 and axially inwardly extending teeth 166 that will engage into the soft tissue 160 and hold it securely against the bone. A separate driver 161 is provided to install washer 162 over post 130. Driver 161 includes a distal end 163 having a flange 165 for engaging washer 162. Driver 161 also includes a central aperture 167 for receiving post 130 therein. Driver 161 forces washer 162 over post 130 in the direction of arrows 169 in FIG. 14. Once the tissue 160 is held against the bone on the post 130 with the washer 162, the excess or outer end of the post 130 can be clipped off as shown in FIG. 15 by a shear-action cutter as indicated at 170. The resultant product is shown in FIG. 16.

The anchor 16a and post 130 may be made from a plastic material such as discussed previously while the washer 162 may also be made from a plastic material capable of securing itself against the teeth 150 and to engage into the soft tissue 160. The anchor 16a is designed such that, with the threading and insertion features discussed above, the post 130 will be securely fastened in the bone for holding the soft tissue 160.

It will be appreciated that the suture 20 in FIGS. 1 and 2 and the post 130 in FIG. 12 are examples of means for engaging the soft tissue and holding the soft tissue relative to the anchors 16, 16a with which they are provided. It will also be appreciated that a number of different types of engaging means may be provided on an anchor of the type illustrated and discussed herein. Once the anchor 16 or 16a is securely fastened into the bone, any number of means for engaging soft tissue may be attached to or provided as part of the anchor. It will also be appreciated that the driver 10 may be made from metal and, in fact, sterilized and reused if that is a desired feature.

What is claimed is:

1. A preassembled disposable driver and suture anchor for threaded engagement into a bone to provide an attachment point for soft tissue, comprising: an anchor being formed to have an externally threaded body portion for engaging the bone, a distal end portion, and a proximal end portion such that, when the anchor is threaded into an opening in a bone, the distal end portion is adjacent a bottom of the opening and the proximal end portion is adjacent a mouth of the opening, a suture attached to said anchor having free ends extending outwardly from the bone opening, said driver being elongated and having a distal end means for engaging the proximal end of said anchor and a proximal end for gripping by the surgeon, said driver also having means for receiving the suture which extends away from said anchor, at least a portion of the distal end means of said driver at the proximal end of the anchor when the anchor and the driver are assembled being radially enlarged relative to the body portion of the anchor to engage the bone surrounding the mouth of the opening to limit the internal advancement of the driver such that rotation of the driver causes no axial movement between the driver and anchor until the distal end means engages the bone surrounding the mouth of the opening whereupon continued rotation of the driver produces relative axial movement between the driver and anchor to provide continued threading of the anchor into the bone by the driver and subsequently separation of the anchor from the driver.

2. The apparatus of claim 1, wherein the proximal end of the anchor is configured to form a male head, and the distal end means of the driver is formed to include a female socket opening configured to receive the male head to provide the means for engaging the proximal end of said anchor.

3. The apparatus of claim 2, wherein the male head and the female socket opening have a square shape.

4. The apparatus of claim 3, wherein the male head includes four corners which are each threaded.

5. The apparatus of claim 2, wherein the threaded body portion of the anchor includes threads having a major diameter and a minor diameter, the head of the anchor having a diameter larger than the minor diameter of the threads.

6. The apparatus of claim 1, wherein the driver includes means for holding the free ends of the suture in tension to hold the anchor on the driver.

7. The apparatus of claim 1, wherein the anchor is formed to include first and second passageways extending longitudinally from the distal end of the anchor to the proximal end of the anchor to provide a web therebetween at the distal end of said anchor, and wherein the suture is threaded through the first passageway of the anchor over the web and back through the second passageway so that the free ends of the suture extend away from the distal end of the anchor.

8. The apparatus of claim 7, wherein the suture is movable in the first and second passageways to equalize a load on the anchor.

9. The apparatus of claim 1, wherein the anchor is made from a plastic material.

10. The apparatus of claim 1, wherein the anchor is made from an absorbable plastic material.

11. The apparatus of claim 1, wherein the anchor is absorbable.

12. The apparatus of claim 1, wherein the suture, when tensioned, applies a compressing force along a longitudinal axis of the anchor to expand the anchor radially outwardly within the opening of the bone to increase a retention force of the anchor in the bone.

13. The apparatus of claim 1 for use with a bone having a countersink surrounding the opening, and wherein the driver includes a conically shaped distal end located adjacent the anchor, the conically shaped distal end being configured to engage the countersink to separate the driver from the anchor.

14. The apparatus of claim 1, wherein the longitudinally extending means for receiving the suture includes a longitudinally extending slot for receiving the free ends of the suture.

15. A preassembled disposable driver and suture anchor for threaded engagement into a drilled and threaded opening in a bone to provide an attachment point for soft tissue to the bone with the opening deeper than the axial length of said anchor, comprising: an anchor being formed to have an externally threaded body portion for engaging the bone, distal end portion, and a proximal end portion such that, when the anchor is threaded into the threaded opening in the bone, the distal end portion is adjacent and spaced apart from the bottom of the opening leaving an internal cavity and the proximal end portion is adjacent a mouth of the opening, said anchor also having a pair of suture openings extending longitudinally from the proximal end to the distal end, a suture extending into one of said pair of openings into the internal cavity and back out through the other of said pair of openings to have opposite free ends extending outwardly away from the proximal end of the anchor and movable within the pair of openings to equalize the tension in the suture when a soft tissue load is placed on the suture, an elongated driver having a distal end including means for drivingly engaging the proximal end of said anchor and a proximal end for gripping by the surgeon and wherein the driver has an enlarged distal end at the proximal end of the anchor when the anchor and the driver are connected wherein the driving connection causes the insert to automatically move into the bone away from the driver as the driver rotates the insert toward the bottom of the opening in the bone.

16. The apparatus of claim 15, wherein the driver is formed to include a longitudinally extending opening for receiving the free ends of the suture therein, the distal end portion of said driver being radially enlarged relative to the anchor to engage the bone surrounding the mouth of the opening to limit the internal advancement of the driver such that further rotation and threading of the anchor into the bone by the driver will separate the anchor from the driver.

17. The apparatus of claim 15, wherein the proximal end of the anchor is configured to form a male head, and the distal end of the driver is formed to include a female socket opening configured to receive the male head to provide the means for engaging the proximal end of said anchor.

18. The apparatus of claim 17, wherein the male head and the female socket opening have a square shape.

19. The apparatus of claim 15, wherein the driver includes means for holding the free ends of the suture in tension to hold the anchor on the driver.

20. The apparatus of claim 15, wherein the anchor is made from a plastic material.

21. The apparatus of claim 15, wherein the anchor is made from an absorbable plastic material.

22. The apparatus of claim 15, wherein the anchor is absorbable.

23. The apparatus of claim 15, wherein the suture, when tensioned, applies a compressing force along a longitudinal axis of the anchor to expand the anchor radially outwardly within the opening of the bone to increase a retention force of the anchor in the bone.

24. A driver suture anchor for threaded engagement into an opening in a bone to provide an attachment point for soft tissue to the bone and the driver therefor, comprising:

an anchor with an externally threaded body portion for engaging the bone, the body portion having a distal end, a proximal end, first and second passageways extending longitudinally from the distal end of the anchor to the proximal end of the anchor to provide a web therebetween at the distal end of the anchor;

a suture extending through the first passageway of the anchor over the web and back through the second passageway so that free ends of the suture extend away from the proximal end of the anchor, the suture being movable in the passageways; and an elongated driver having a distal end formed to include means for engaging the proximal end of the anchor and a proximal end for gripping by the surgeon to rotate the driver and the anchor to thread the anchor into the bone and wherein the driver has an enlarged distal end at the proximal end of the anchor when the anchor and driver are connected wherein rotation of the driver by the surgeon causes concurrent rotation of driver and anchor into the bone without axial movement therebetween and wherein continued rotation of the driver and anchor causes relative axial movement of the anchor with respect to the driver when the driver engages the bone, with the relative axial movement continuing with conjoint rotation until the anchor is separated from the driver at a location completely within the bone.

25. The apparatus of claim 24 wherein the driver is formed to include a longitudinally extending slot for receiving the free ends of the suture therein.

26. The apparatus of claim 24 wherein the distal end of the driver has a larger diameter than a diameter of the body portion of the anchor so that the driver engages the bone surrounding a mouth of the opening to block internal advancement of the driver so that further rotation and threading of the anchor into the bone by the driver will automatically separate the driver from the inserted anchor.

27. The apparatus of claim 24 wherein the proximal end of the anchor is configured to form a male head, and the distal end of the driver is formed to include a female socket opening configured to receive the male head to provide the means for engaging the proximal end of said anchor.

28. The apparatus of claim 24 wherein the driver includes means for holding the free ends of the suture in tension to hold the anchor on the driver.

29. The apparatus of claim 24, wherein the suture is movable in the first and second passageways to equalize a load on the anchor.

30. The apparatus of claim 24, wherein the anchor is made from a plastic material.

31. The apparatus of claim 24, wherein the anchor is made from an absorbable plastic material.

32. The apparatus of claim 24, wherein the anchor is absorbable.

33. A method for attaching soft tissue to a bone using an anchor having an externally-threaded body portion, the method comprising the steps of:

(a) drilling a hole into the bone to a first predetermined depth with a spot faced, dressed area cut in the bone about an outer periphery of the hole;

(b) tapping the hole to provide internal threads to a second predetermined depth less than the first predetermined depth;

(c) inserting the externally threaded anchor, having an axial length less than the first predetermined depth and a threaded length less than the second predetermined depth, into the hole so that a distal end of the anchor is spaced apart from a bottom of the hole to provide an internal cavity and a proximal end of the anchor is disposed adjacent a mouth of the hole, the anchor carrying means for engaging the soft tissue to position the soft tissue against the spot faced, dressed area around the hole; and wherein the inserting step uses a driver to rotate the anchor, the driver having a larger diameter than the anchor so that the driver engages the countersink to block internal advancement of the driver and so that further rotation and threading of the anchor into the bone by the driver automatically separates the driver from the inserted anchor.

34. The method of claim 33, wherein the drilling step forms a countersink surrounding a mouth of the hole and the dressed area is cut around the countersink so that the proximal end of the anchor is disposed generally within the countersink.

35. The method of claim 34, wherein the engaging means includes a spike formed on the proximal end of the anchor to extend outwardly from the hole and penetrate the soft tissue.

36. The method of claim 34, wherein the engaging means includes a suture coupled to the anchor.

37. The method of claim 34, wherein the anchor is absorbable.

38. The method of claim 34, wherein the anchor is made from a plastic material.

39. A method for attaching soft tissue to a bone using a suture anchor having an externally threaded body portion for engaging the bone, the body portion having a distal end, a proximal end, first and second passageways extending longitudinally from the distal end of the anchor to the proximal end of the anchor, the method comprising the steps of:

(a) drilling a hole into the bone to a first predetermined depth with a dressed area cut in the bone about an outer periphery of the hole to provide a contact surface for the soft tissue;

(b) tapping the hole to provide internal threads;

(c) providing a suture loosely threaded through the first passageway formed in the anchor, over a web of material at the distal end of the anchor between the first and second passageways, and back through the second passageway formed in the anchor so that free ends of the suture extend away from the proximal end of the anchor;

(d) inserting the anchor into the hole so that the distal end of the anchor is adjacent a bottom of the hole, the proximal end of the anchor is adjacent an opening of the hole and the free ends of the suture extend outwardly from the hole;

(e) attaching the free ends of the suture to the soft tissue to position the soft tissue against the dressed area around the hole; and wherein the inserting step uses a driver to rotate the anchor, the driver having a larger diameter than the anchor so that the driver engages the countersink to block internal advancement of the driver and so that further rotation and threading of the anchor into the bone by the driver automatically separates the driver from the inserted anchor.

40. The method of claim 39, wherein the drilling step forms a countersink surrounding a mouth of the hole and the dressed area is cut around the countersink so that the proximal end of the anchor is disposed generally within the countersink.

41. The method of claim 39, wherein the anchor is absorbable.

42. The method of claim 39, wherein the anchor is made from a plastic material.

* * * * *